United States Patent [19]

Skobelev et al.

[11] Patent Number: 5,586,872
[45] Date of Patent: Dec. 24, 1996

[54] ADJUSTABLE PERISTALTIC PUMP

[76] Inventors: Valery V. Skobelev, ulitsa Menzhinskogo, 10, kv. 232; Mikhail A. Slivin, prospekt Krasnoyarsky rabochy, 191 A, kv. 36; Evgeny A. Selezov, ulitsa K. Marxa, 88, kv. 37; Viktor G. Kabakov, pereulok Rechnoi, 1, kv. 33; Gennady S. Puzikov, ulitsa Mechnikova, 12, kv. 61, all of Krasnoyarsk, Russian Federation

[21] Appl. No.: 232,096

[22] PCT Filed: Sep. 2, 1992

[86] PCT No.: PCT/RU92/00171

§ 371 Date: Apr. 29, 1994

§ 102(e) Date: Apr. 29, 1994

[87] PCT Pub. No.: WO94/05345

PCT Pub. Date: Mar. 17, 1994

[51] Int. Cl.$^6$ .................................................. F04B 43/08
[52] U.S. Cl. ............................................................. 417/477.8
[58] Field of Search .................................. 417/474, 475, 417/476, 477.1, 477.3, 477.7, 477.8, 477.9, 477.12; 604/153

[56] References Cited

U.S. PATENT DOCUMENTS

| | | | |
|---|---|---|---|
| 2,123,781 | 7/1938 | Huber | 417/477.12 |
| 2,831,437 | 4/1958 | Cromwell et al. | 417/477.5 |
| 2,987,004 | 6/1961 | Murray | 417/475 |
| 2,987,005 | 6/1961 | Dann | 417/477.7 |
| 3,447,478 | 6/1969 | Clemens | 417/477.8 |
| 3,554,674 | 1/1971 | Huret | 417/477.3 |
| 3,726,613 | 4/1973 | von Casimir | 417/477.1 |
| 3,927,955 | 12/1975 | Spinosa et al. | 417/477 |
| 4,012,177 | 3/1977 | Yakich | 417/477 |
| 4,205,948 | 6/1980 | Jones | 417/477.8 |
| 4,363,609 | 12/1982 | Cosentino | 417/477.7 |
| 4,484,864 | 11/1984 | Michel | 417/477.8 |
| 4,568,255 | 2/1986 | Lavender et al. | 417/477.8 |
| 4,997,347 | 3/1991 | Roos | 417/475 |
| 5,372,486 | 12/1994 | Wehling | 417/477.8 |

FOREIGN PATENT DOCUMENTS

| | | | |
|---|---|---|---|
| 1035679 | 4/1953 | France | 417/477 |
| 2162998 | 12/1971 | Germany | 417/477 |
| 2217787 | 10/1973 | Germany | 417/477 |
| 59-74387 | 4/1984 | Japan | 417/477 |
| 59-165883 | 9/1984 | Japan | 417/477 |
| 0211678 | 8/1989 | Japan | 418/45 |
| 237346 | 6/1969 | U.S.S.R. | |
| 1408105 | 7/1988 | U.S.S.R. | 417/477 |
| 1643783 | 4/1991 | U.S.S.R. | 417/477.13 |
| 2230301 | 10/1990 | United Kingdom | 417/474 |

*Primary Examiner*—Timothy Thorpe
*Assistant Examiner*—Peter G. Korytnyk
*Attorney, Agent, or Firm*—Keck, Mahin & Cate

[57] ABSTRACT

The invention relates to a pump for biological fluids, for example for blood transference by pump. The pump according to the invention comprises a housing (1) in which there are placed at least one resilient tube (3) for passing biological fluid, and an operating head (5) rotated in the direction of fluid transference and including at least one roller member (6) to bear against the tube (3), said roller member (or each roller member) comprising at least two rollers (7,8) positioned in series so that the roller (7) of said roller member which is preceding in the direction of the operating head rotation allows greater tube (3) aperture than does the roller (8) of the same member (6) that follows. The pump has simple and convenient means for adjusting the degree of compressing the tube (3) by the rollers (7,8) and ensures blood transfusion causing practically no damage to the blood cells.

5 Claims, 6 Drawing Sheets

ADJUSTABLE PERISTALTIC PUMP

FIELD OF THE INVENTION

The present invention relates to a pump for transferring biological fluids, comprising a housing which includes at least one resilient tube. Biological fluid transferred by pump is passed through the at least one tube, and an operating head which is rotatable in the direction of fluid transference contains at least one roller member to bear against the tube.

BACKGROUND OF THE INVENTION

Pumps of such type have been known in the art for a considerable time and are used at present in medicine for transferring biological fluids by pump.

Operation of these pumps is based on the principle that while an operating head is rotated, its roller member (or members) travels along the resilient tube in the direction of fluid transference, compressing the tube at the point of its contact with the rollers. Displacement of a contracted section of the tube's aperture results in pushing through the fluid along the tube in a manner which is similar to pushing through, for example, food during peristalsis (periodic wave-like contraction) of intestines. Accordingly, in view of their operating principle, the pumps of this type are also called "peristaltic".

The major task to be solved by such pumps consists in ensuring effective transference of blood at a required flow rate (volume to time), minimally affecting the transferred biological fluid. This latter condition is especially important because blood contains form elements such as erythrocytes, which are easily destructible by mechanical actions (impacts, shaking, vibration, etc.). Destruction of blood form elements (also known as "hemolysis") unavoidably arising during transference of blood to a patient, leads particularly to such an undesirable phenomenon as after-transfusion fever, which is a result of the human body's reaction to dissolved substances in blood which have separated from erythrocytes and other form elements destroyed during blood transference.

This reaction of the patient's body is stronger when the amount of blood subject to transference to the patient is greater. Thus, the more dramatic is the condition of a person and the greater is the quantity of blood required for transfusion, then the more dangerous is the undesirable phenomenon. This problem is substantially solved by the pumps of above type in which blood transference is performed without abrupt mechanical actions, i.e., peristaltically. The problem, however, has not been completely eliminated until now, and even while using the most advanced blood transfusion apparatus, medical personnel now and again register a patient's fever condition after transferring considerable quantities of blood, and additional efforts must be made to eliminate these after effects.

Specifically, in the description in U.S. Pat. No. 3,447,478 (Int.Cl.F 04 B 43/08), there is disclosed a "peristaltic" pump for blood transfusion, which includes features in which some of its roller members completely pinch the tube for transferring fluid, other roller members serving to adjust the amount of transferred fluid per unit of time by incomplete contraction of the tube aperture.

In the description of U.S. Pat. No. 4,012,177, there is disclosed a similar pump which has the same application and is provided with an improved construction of the tube allowing hemolysis during blood transference through the tube to be reduced.

None of the prior art pumps of the peristaltic type ensure complete elimination of hemolysis, and the pumps mentioned hereinabove are no exception. There still remains an urgent need to create a pump capable of transferring blood without substantial destruction of form elements ("hemolysis").

Additionally, the known pumps require relatively frequent replacement of the tube due to wear which means additional problems to the user.

SUMMARY OF THE INVENTION

Thus, the object of the present invention is to create such a peristaltic pump which would ensure effective transference of blood, minimally affecting its form elements.

Another object of the invention resides in solving the task of improving reliability of the pump and reducing the rate of its wear.

These objects are accomplished as follows. The pump of the above type according to the invention is distinctive from the prior art technical solution in that each roller member comprises at least two rollers placed in series so that the roller which is preceding in the direction of rotor rotation allows a greater aperture of the tube for transference in comparison with the roller of the same roller member which follows.

These distinctions permit blood transfusion with an incomplete pinching of the resilient tube and, hence, without destruction of form elements of blood and without reducing the pump's flow rate. The first hydraulic wave formed by the first roller of the roller member creates in front of the first roller an elevated pressure region, the value of such pressure being less than in front of the second roller, which provides a smaller aperture of the resilient tube. Thus, smoothly obtained build-up of pressure secures minimal damage to blood form elements.

Preferably, between the tube and roller members there is placed a gasket of resilient material, one side of the gasket being the rolling surface of the rollers, another side bearing on the tube.

The roller members can be mounted immediately on the operating head; however, in the preferred embodiment the rollers are connected to the operating head by means of a carrier.

The user will find it convenient if the pump is provided with means for adjusting the degree of compression of the tube, these means preferably being mounted on the operating head. Such means for adjusting the tube compression degree can comprise a turnable and retainable eccentric placed coaxially with the operating head and coupled with the roller member or members.

Means for retaining the eccentric usually include simple arrestment members, e.g., pins or balls.

The roller of the roller member which is preceding in the direction of rotation is preferably provided with another (second) means for adjusting the degree of compression of the tube by changing the position of this roller in relation to the carrier. In this embodiment, the second means can be most conveniently arranged in the form of a figurate or straight slot in the carrier to receive the axis of the roller preceding in the direction of rotation.

The resilient gasket usually is formed of a belt made of elastic material, though it can be of annulus or cylinder shape.

It is clear that the concept of the present invention can be developed to include a greater number of operating heads in one pump to provide a blood transfusion station for several patients. An example of such development of the invention is given below, wherein the pump of the invention comprises two tubes and two operating heads.

BRIEF DESCRIPTION OF THE DRAWINGS

The invention is further illustrated by non-limiting embodiments with reference to the drawings, wherein.

DETAILED DESCRIPTION OF THE PREFERRED EMBODIMENTS

Figure 1:
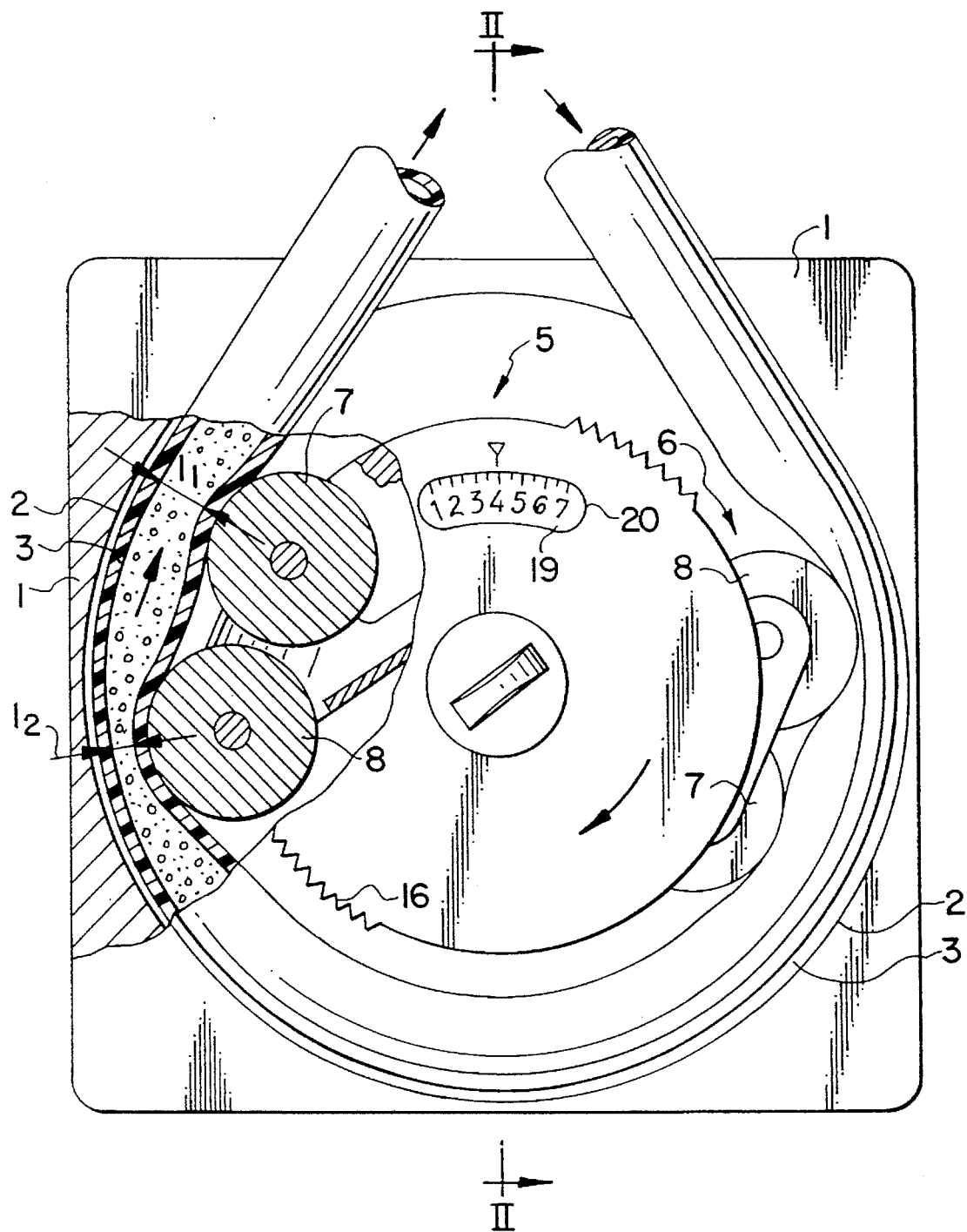
FIG. 1 is a schematic general view of a pump according to the invention, in partial cross-section, with side cover removed.
Figure 2:
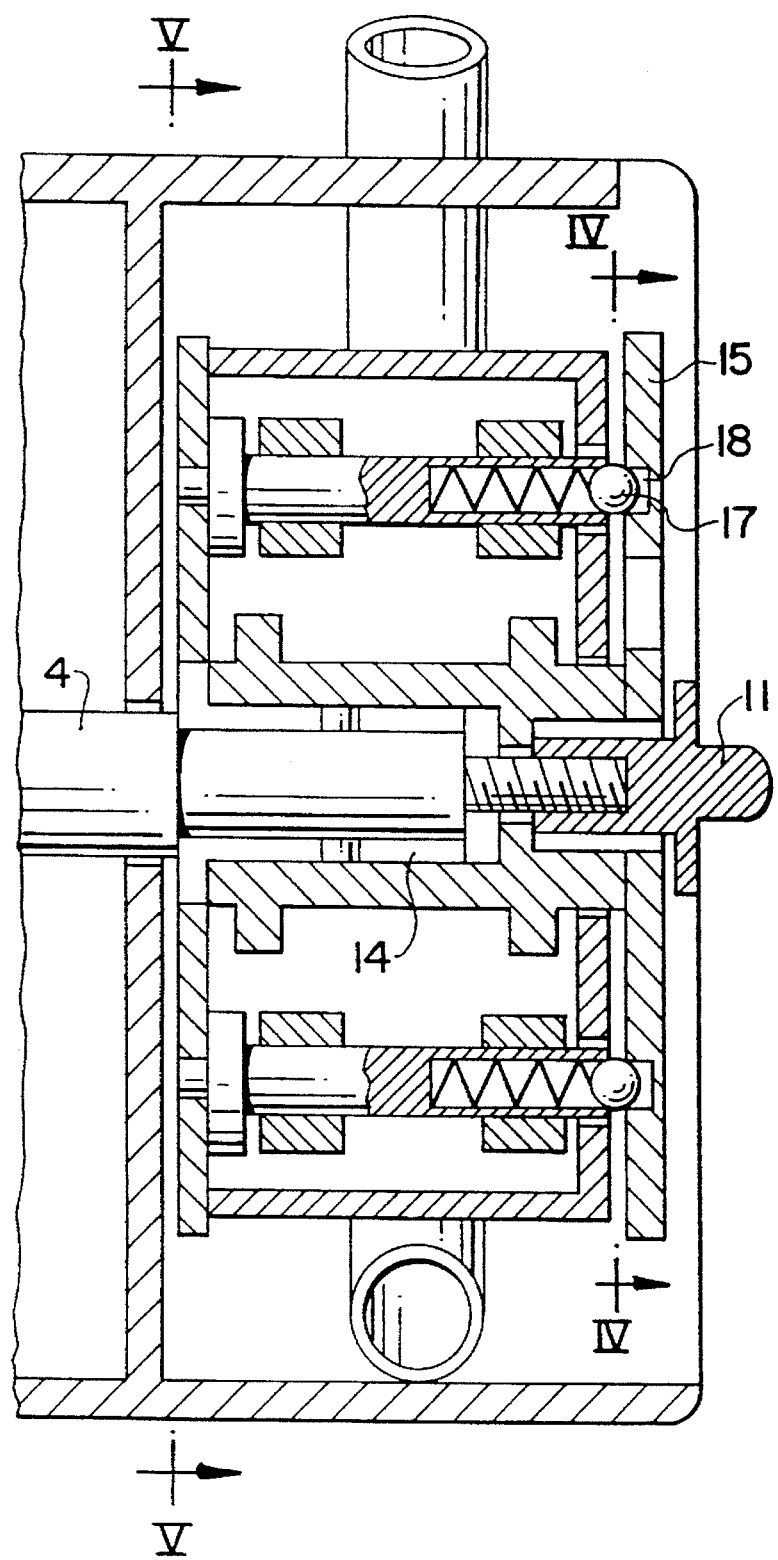
FIG. 2 is a cross-section along line II—II of FIG. 1.

FIG. 1 is a schematic general view of a pump according to the invention, and FIG. 2 is cross-section of the same. From these drawings it becomes apparent that inside a housing (1) having a cylinder bore (2) there is placed a resilient tube (3) through which biological fluid (blood) is passed, the tube being made of material which is traditional in such devices, bearing no effect on the transferred fluid and capable of multiple sterilizations, for example, of silicon.

To reliably retain the tube (3) in a fixed position, there are provided in the housing (1) suitable for the purpose traditional means, for example, recesses or grooves, which correspond to the tube dimensions and are provided by boring or otherwise. In the inner space of the housing (1), an operating head (5) is rotatably mounted on a shaft (4) in the direction of fluid transference (shown in the drawing as clockwise).

The operating head (5) is provided in the present example with two symmetrically placed roller members (6).

According to the invention, each roller member (6) comprises at least two rollers (7 and 8) placed in series so that the preceding roller (7) or the so-called first roller in the direction of the operating head (5) rotation allows greater aperture of the tube (3) than that allowed by the following or the so-called second roller (8) of the same roller member. This feature which determines the major concept of the invention, has been realized in the embodiment shown in FIG. 1, by a corresponding arrangement of the first and the second rollers (7, 8), axes of levers (9) of carrier (10) connecting these rollers to the rotatable operating head. The presence of the carrier (10) is also preferable to facilitate adjustment of distance between the roller members (6) and the operating head (5) to enable the rollers (7, 8) to perform the required reduction of the tube (3) aperture at the point of contact, and to ensure that distance $1_1$ is greater than distance $1_2$.

However, it is easy to imagine a pump according to the invention in which the condition of changing the tube (3) aperture ($1_1 > 1_2$) would be carried out differently, e.g., owing to different diameter of the rollers (7, 8). Such alternatives of construction are not described here in greater detail because they remain within the scope of the invention and are quite obvious for a person specializing in the art.

In exactly the same manner it is possible to use even more than two rollers in each roller member, since even with a greater number of rollers, the main condition ($1_1 > 1_2$) is quite realizable. The only criterion when increasing the number of rollers in each roller member (up to three and more) is the expediency of such modernization in view of the structural features of the specific pump (e.g., its dimensions).

Figure 5:
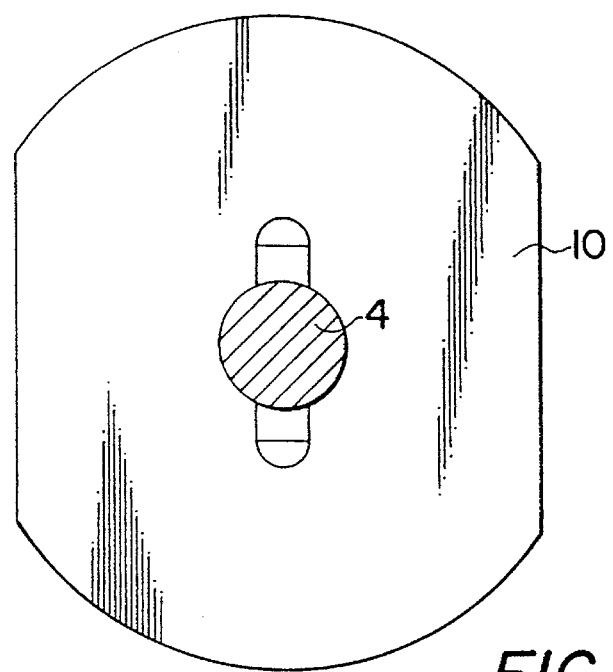
FIG. 5 is a carrier back view along line V—V of FIG. 2.

The operating head (5) is removably mounted on the shaft (4) and fixed to it by the aid of a threaded member (nut 11) and has a slot (12) (see FIG. 5) for transferring a turning moment of the operating head to the carrier (10).

Figure 3:
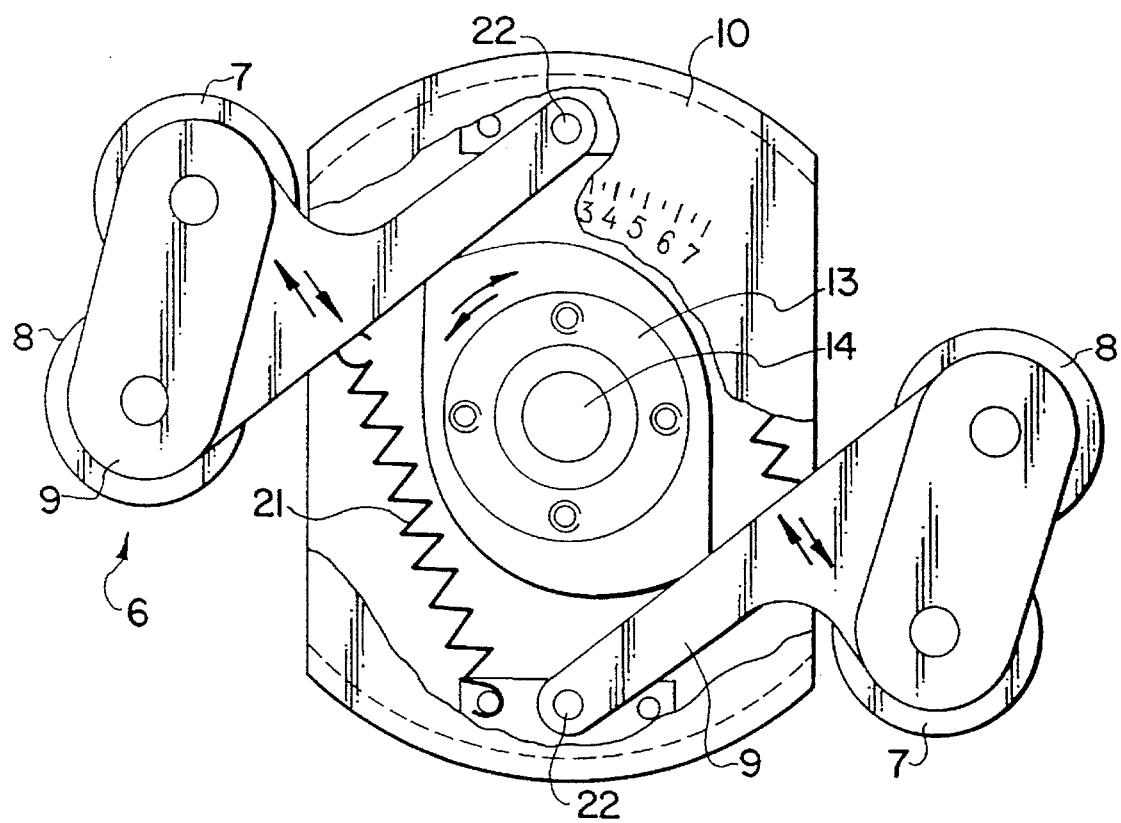
FIG. 3 is an expanded view, in partial cross-section, of an eccentric mechanism of the means for adjusting the degree of compression of the tube by the rollers.
Figure 4:
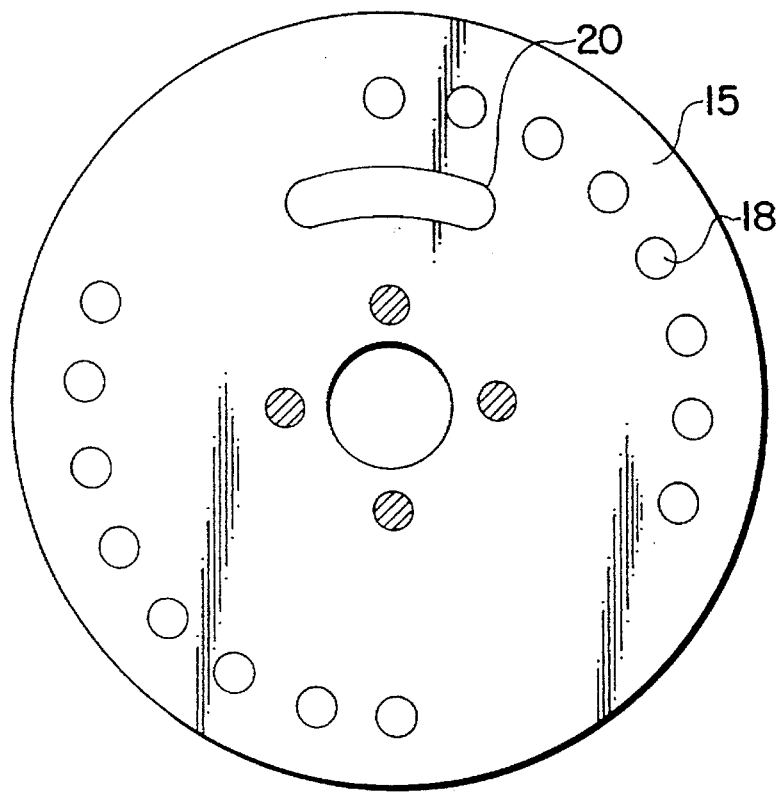
FIG. 4 is a dial suitable for manual adjustment of the eccentric position, viewed along line IV—IV of FIG. 2.

FIG. 3 shows a means for adjusting the tube (3) compression degree secured by rollers (7, 8), which has an eccentric mechanism, including an eccentric (13) mounted coaxially to the operating head (5), and a means for its rotating and retaining. The eccentric (13) can swing over its own axis (14) to make a certain angle by the aid of a manual adjustment dial (15) having finger patterns (16) to facilitate its employment by the user (see FIG. 1) and to be retained in this position with the help of balls (17) entering the openings (or depressions) (18) of a retaining disc (15), as shown in FIGS. 2 and 4. The retaining openings (18) are distributed over the disc (15) circumference at a certain interval, e.g., at such interval which corresponds to radial displacement of the roller member (6) or 0.15 mm. Position of the eccentric (13) as well its change and, hence, the change of the distance from the roller member (6) to the inner surface (2) of the housing (1) which is responsible for the tube (3) compression degree, are monitored by the aid of a scale (19) which is visible through a window (20) of the disc (15).

The turnable eccentric (cam) (13) interacts with levers (9) of the roller members (6). The levers are spring-loaded (by springs 21) and rotatably mounted on the carrier (10) on axes (22). Thus, when turning the retaining disc (15) by a desired angle controlled by means of the scale (19) which is visible through the window (20) of the disc (15), the eccentric (13) makes a turn, and the levers (9) are displaced thereby securing the required change of the tube (3) compression degree by the aid of the rollers (7, 8).

Figure 6:
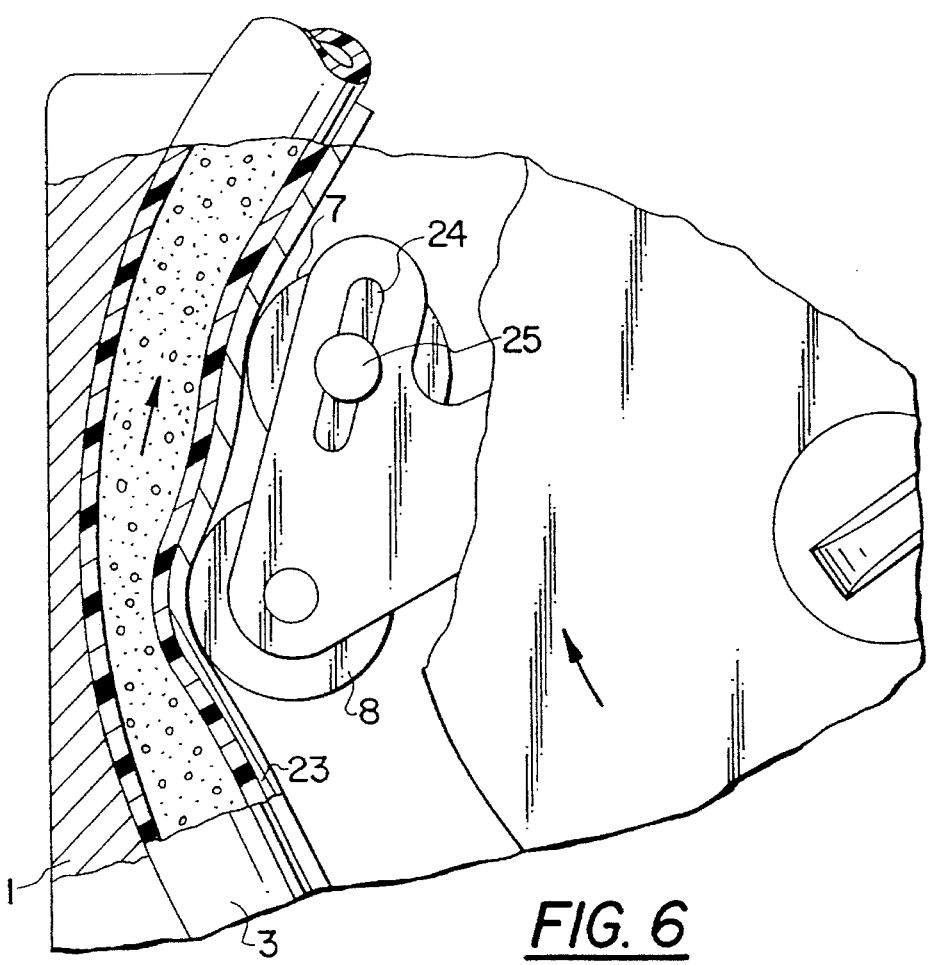
FIG. 6 shows the second means for adjusting the position change of the preceding roller in the direction of rotation.
Figure 8:
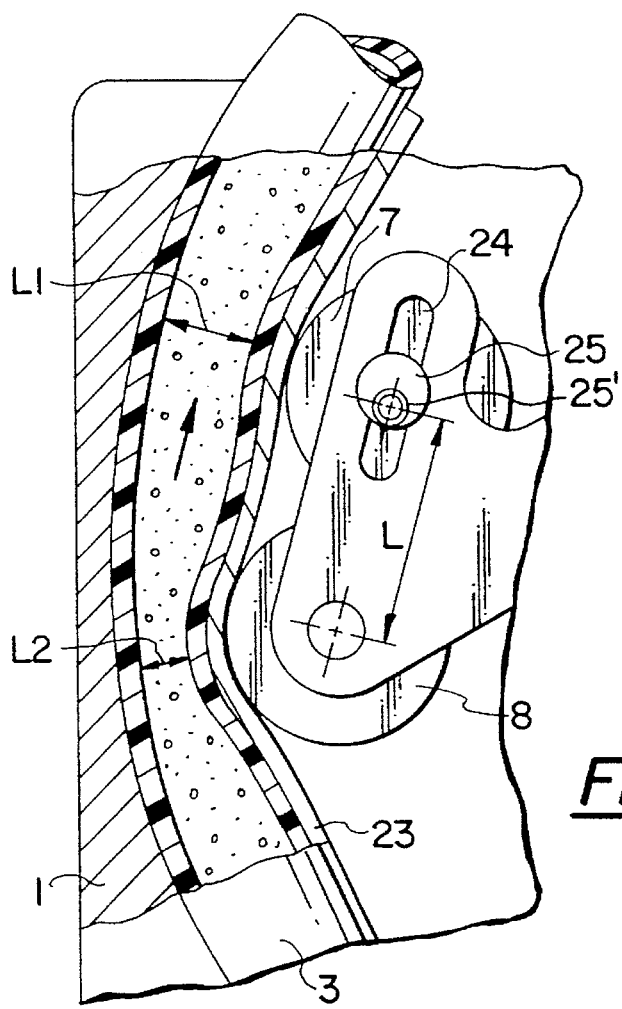
FIG. 8 is a view similar to FIG. 6 showing an eccentric for adjusting the position of the preceding roller.
Figure 9:
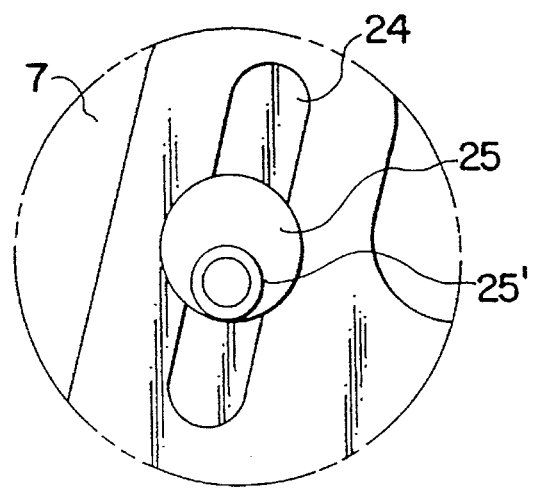
FIG. 9 is a detail of FIG. 8.

FIG. 6 shows an alternative embodiment of the invention, which is provided with a gasket (23) and the second means for adjusting the position of the first roller (7). Between the tube (3) and the roller members (6) there is placed the gasket (23) made of elastic material, one side of the gasket being the rolling surface of the rollers (7 and 8), another side bearing on the tube (3). The gasket helps to reduce wear of the tube (3) as it excludes development of tensile forces which would expand the tube and ensures a more continuous wave-like deformation of the tube (3) walls when the rollers roll on the tube. The second (additional) means for adjusting the position of the first roller (7) comprises a slot (24) obtained in the lever (9). The slot (24) receives the axis (25) of the first roller (7) with a possibility of retaining it in the desired position. The member (25) can also be embodied in the form of an eccentric (25') as shown in FIGS. 8 and 9, which gives the user additional possibilities in adjusting the pump. The direction of the slot (24), which is sloping and not radial as in U.S. Pat. No. 3,447,478, offers additional advantages by allowing the user to achieve greater accuracy of adjustment. In addition, in the pump of the invention, this second means of adjustment also avails of such an advantage that the adjustment of the first roller (7) position without changing the second roller (8) position allows to choose the value $\Delta 1$ ($\Delta 1 = 1_1 - 1_2$) for creating a laminar flow of fluid in the tube without vortices and cavitation in the zone where the tube is compressed by the rollers (7, 8). The means of adjustment shown in the description permit widening of the scope of application of the pump according to the invention, making it more versatile owing to the fact that now it becomes possible to easily regulate the pump without changing the fluid viscosity factor, the flow rate, as well as when replacing the tube which can possibly result in the change of the tube resilience, its passable section, etc.

Figure 7:
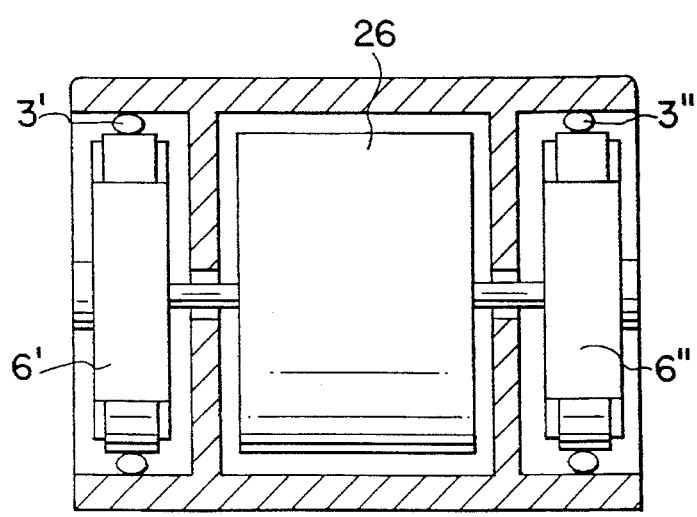
FIG. 7 is a schematic view of an alternative embodiment of the pump according to the invention as a station with two tubes and two operating heads and having a common drive.

Finally, FIG. 7 is a schematic view of a blood transfusion station according to the present invention. The central drive (26) rotates the two operating heads (6' and 6''') placed symmetrically to transfer blood through the tubes (3' and 3''). It is clear that the operating heads and the tubes can number more than two. As the respective housing and drive embodiments are already beyond the scope of the inventive concept, their details are not considered here.

It will be noted that the above exemplary embodiments are not limiting the present invention which can be developed by the specialist in the art without deviation from the essence of the invention cited in the claims attached hereto.

We claim:

1. A pump for biological fluids comprising a housing which includes:

a resilient tube for passing through biological fluid, and an operating head which is rotatable in the direction of fluid transference by pump and which contains at least one roller member for bearing against said tube, wherein:

the at least one roller member comprises at least two rollers placed in series so that a roller of said roller member which is preceding in a direction of the operating head rotation has a greater aperture of said tube for transference in comparison with the roller of the same member which follows, and the pump is provided with a means for adjusting the degree of compression of said tube using the rollers, said means being mounted in the region of the operating head, wherein, said means for adjusting the degree of compression of the tube comprises a turnable and retainable eccentric placed coaxially with the operating head and coupled with at least one said roller member.

2. The pump of claim 1, wherein the means for retaining said eccentric comprises arrestment members.

3. The pump of claim 1 wherein the roller of said roller member which is preceding in the direction of rotation has a second adjustment means for changing the position of said roller in relation to the carrier lever.

4. The pump of claim 3, wherein said second means for adjusting the degree of compression of said tube is arranged in the form of a figurate or straight slot in the carrier lever to receive the axis of the roller preceding in the direction of roller movement.

5. The pump of claim 3, wherein said second adjustment means comprises an eccentric.

* * * * *